United States Patent [19]

Sakaniwa et al.

[11] Patent Number: 5,159,622
[45] Date of Patent: Oct. 27, 1992

[54] X-RAY FLUOROSCOPIC IMAGING APPARATUS WITH EXTENDED IMAGING SET UP RANGE

[75] Inventors: Hiroshi Sakaniwa, Ootawara; Satoshi Ohta, Imaichi; Katsuhiko Koyama, Tokyo, all of Japan

[73] Assignee: Kabushiki Kaisha Toshiba, Kawasaki, Japan

[21] Appl. No.: 610,798

[22] Filed: Nov. 8, 1990

[30] Foreign Application Priority Data

Nov. 17, 1989 [JP] Japan .................................. 1-298983

[51] Int. Cl.⁵ ............................................ H05G 1/02
[52] U.S. Cl. ..................................... 378/196; 378/197
[58] Field of Search ........................ 378/197, 196, 195

[56] References Cited

U.S. PATENT DOCUMENTS

| | | | |
|---|---|---|---|
| 4,741,015 | 4/1988 | Charrier | 378/197 |
| 4,868,845 | 9/1989 | Koropp | 378/197 |
| 4,884,293 | 11/1989 | Koyama | 378/197 |
| 4,922,512 | 5/1990 | Lajus et al. | 378/197 |
| 5,038,371 | 8/1991 | Janssen et al. | 378/197 |
| 5,050,204 | 9/1991 | Siczek et al. | 378/197 |

Primary Examiner—Craig E. Church
Attorney, Agent, or Firm—Oblon, Spivak, McClelland, Maier & Neustadt

[57] ABSTRACT

An X-ray fluoroscopic imaging apparatus capable of taking the fluoroscopic images of an arbitrary portion of an object to be examined from all directions without moving the object to be examined itself. The apparatus includes an arm member for supporting a fluoroscopic imaging device to be slidable along a circle centered around an isocenter; a supporting member for supporting the arm member to be rotatable in a vertical plane; and a carrier member for moving the support member in a horizontal plane, and for rotating the supporting member in the horizontal plane around a pivotal center not identical to the isocenter; where the carrier member, the supporting member, and the arm member are controlled such that the fluoroscopic imaging device can effectively be moved among positions distributed spherically around the isocenter, without changing an orientation of the supporting member with respect to the isocenter. The apparatus can also be effective in taking the fluoroscopic images of a region of interest in the object to be examined which requires more than one fluoroscopic imaging operations, without moving the object to be examined itself.

5 Claims, 5 Drawing Sheets

X-RAY FLUOROSCOPIC IMAGING APPARATUS WITH EXTENDED IMAGING SET UP RANGE

BACKGROUND OF THE INVENTION

1. Field of the Invention

The present invention relates to an X-ray fluoroscopic imaging apparatus for examining an object to be examined by taking fluoroscopic images.

2. Description of the Background Art

Several types of an X-ray fluoroscopic imaging apparatus are known conventionally.

One example of such a conventional X-ray fluoroscopic imaging apparatus is shown in FIG. 1, where an X-ray fluoroscopic imaging apparatus 1 is equipped with an approximately C-shaped supporting arm 2 which carries a fluoroscopic imaging device and an X-ray tube on its two opening ends. This C-shaped supporting arm 2 can slide along a circle centered around an isocenter O, in a direction indicated by an arrow A. A stem of this C-shaped arm is supported to be rotatable in a vertical plane, in a direction indicated by an arrow B, by a supporting base 3 attached to a floor. The supporting base 3 itself is also rotatable in a direction indicated by an arrow C in a horizontal plane.

Another example of such a conventional X-ray fluoroscopic imaging apparatus is shown in FIG. 2, where the X-ray fluoroscopic imaging apparatus 4 is equipped with an approximately U-shaped supporting arm 5 which carries a fluoroscopic imaging device and an X-ray tube on its two opening ends. Two legs of this U-shaped supporting arm 5 can reciprocatively slide as indicated by arrows D such that an isocenter O remains on a line joining the fluoroscopic imaging device and the X-ray tube on two opening ends. A stem of this U-shaped arm 4 is supported to be rotatable in a vertical plane, in a direction indicated by an arrow E, by a supporting base 6 attached to a floor.

Still another example of such a conventional X-ray fluoroscopic imaging apparatus is shown in FIG. 3, which differs from the example of FIG. 1 in that, in this conventional X-ray fluoroscopic imaging apparatus 7, the supporting base 9 for supporting the C-shaped arm 8 is attached not to the floor but to the ceiling.

Now, all of these conventional X-ray fluoroscopic imaging apparatus have a problem that, in taking an image of a heart of a patient for instance, due to the lack of enough degrees of freedom for its arm carrying the fluoroscopic imaging device and the X-ray tube, it has been impossible to obtain the X-ray fluoroscopic images from all directions around a region of interest in the object to be examined located at the isocenter O, without changing a position or an orientation of the object to be examined itself.

On the other hand, when the object to be examined is moved to change its position, overlapping of the images before and after the moving occurs on a display, for example for the images of blood vessels, whereas when the object to be examined is moved to change its orientation, a displayed image on a monitor is rotated, and these can give rise to difficulties or errors in the diagnosis using the displayed image.

Moreover, in taking an image of blood vessels in an inferior limb of a patient, because the image cannot be taken completely by a single imaging operation at a single position, it is inevitably necessary to shift the imaging region gradually for several times in a course of successive imaging operations, and in such a case, it has been unavoidable conventionally to move the patient for each imaging, which causes the similar problem associated with the moving of the patient as mentioned above.

SUMMARY OF THE INVENTION

It is therefore an object of the present invention to provide an X-ray fluoroscopic imaging apparatus with an extended imaging set up range which is capable of taking the fluoroscopic images of an arbitrary portion of the object to be examined from all directions, without moving the object to be examined itself.

It is another object of the present invention to provide an X-ray fluoroscopic imaging apparatus capable of taking the fluoroscopic images of a region of interest in the object to be examined which requires more than one fluoroscopic imaging operation, without moving the object to be examined itself.

According to one aspect of the present invention there is provided an X-ray fluoroscopic imaging apparatus, comprising: an arm member for supporting a fluoroscopic imaging device capable of taking a fluoroscopic image of a patient, to be slidable along a circle centered around an isocenter; a supporting member for supporting the arm member to be rotatable in a vertical plane; carrier means for moving the support member in a horizontal plane, and for rotating the supporting member in the horizontal plane around a pivotal center not identical to the isocenter; and means for controlling the carrier means, the supporting member, and the arm member such that the fluoroscopic imaging device can effectively be moved among positions distributed spherically around the isocenter, without changing an orientation of the supporting member with respect to the isocenter.

According to another aspect of the present invention there is provided an X-ray fluoroscopic imaging apparatus, comprising: an arm member for supporting a fluoroscopic imaging device capable of taking a fluoroscopic image of a patient, to be slidable along a circle centered around an isocenter; a supporting member for supporting the arm member to be rotatable in a vertical plane; carrier means for moving the support member in a horizontal plane, along the patient; and means for controlling the carrier means, the supporting member, and the arm member such that the fluoroscopic imaging device can be slid along the patient.

Other features and advantages of the present invention will become apparent from the following description taken in conjunction with the accompanying drawings.

DETAILED DESCRIPTION OF THE PREFERRED EMBODIMENTS

Figure 1:
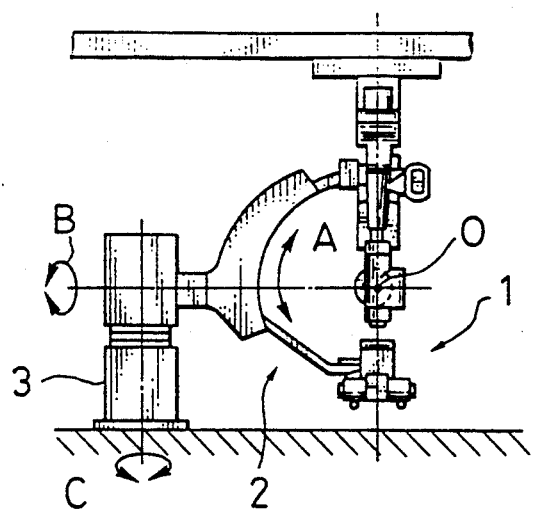
FIG. 1 is a side view of one example of a conventional X-ray fluoroscopic imaging apparatus.
Figure 2:
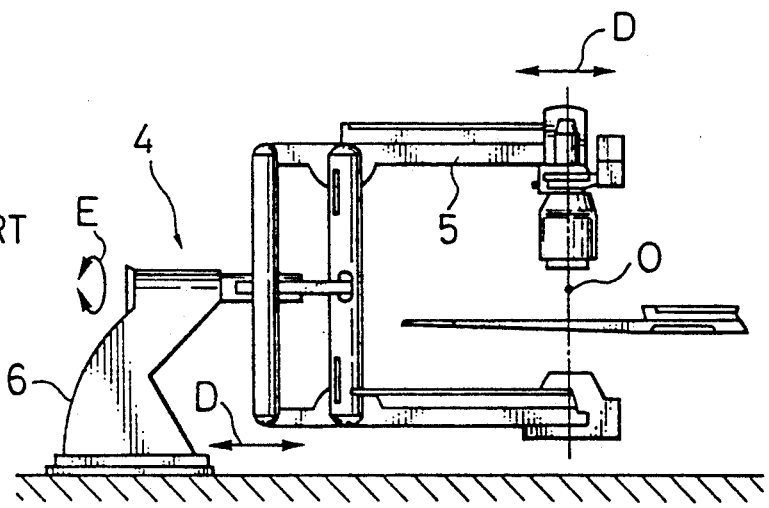
FIG. 2 is a side view of another example of a conventional X-ray fluoroscopic imaging apparatus.
Figure 3:
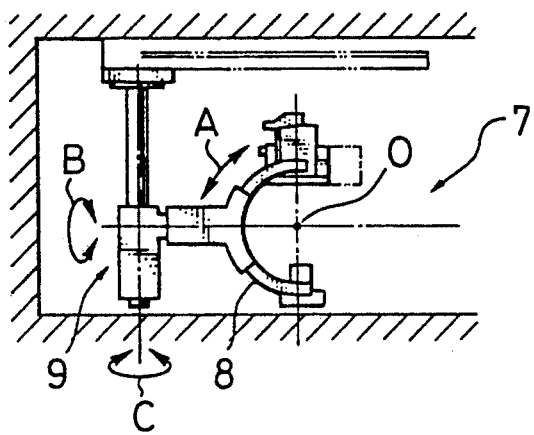
FIG. 3 is a side view of still another example of a conventional X-ray fluoroscopic imaging apparatus.
Figure 4A:
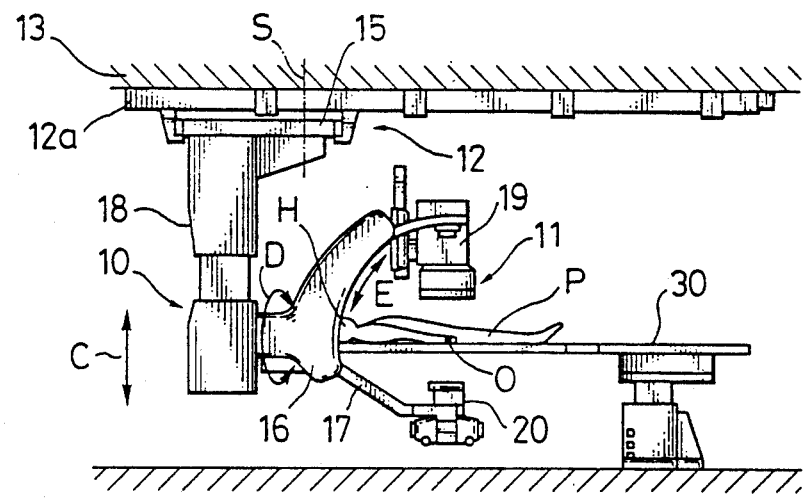
FIG. 4(A) is a side view of one embodiment of an X-ray fluoroscopic imaging apparatus according to the present invention.
Figure 4B:
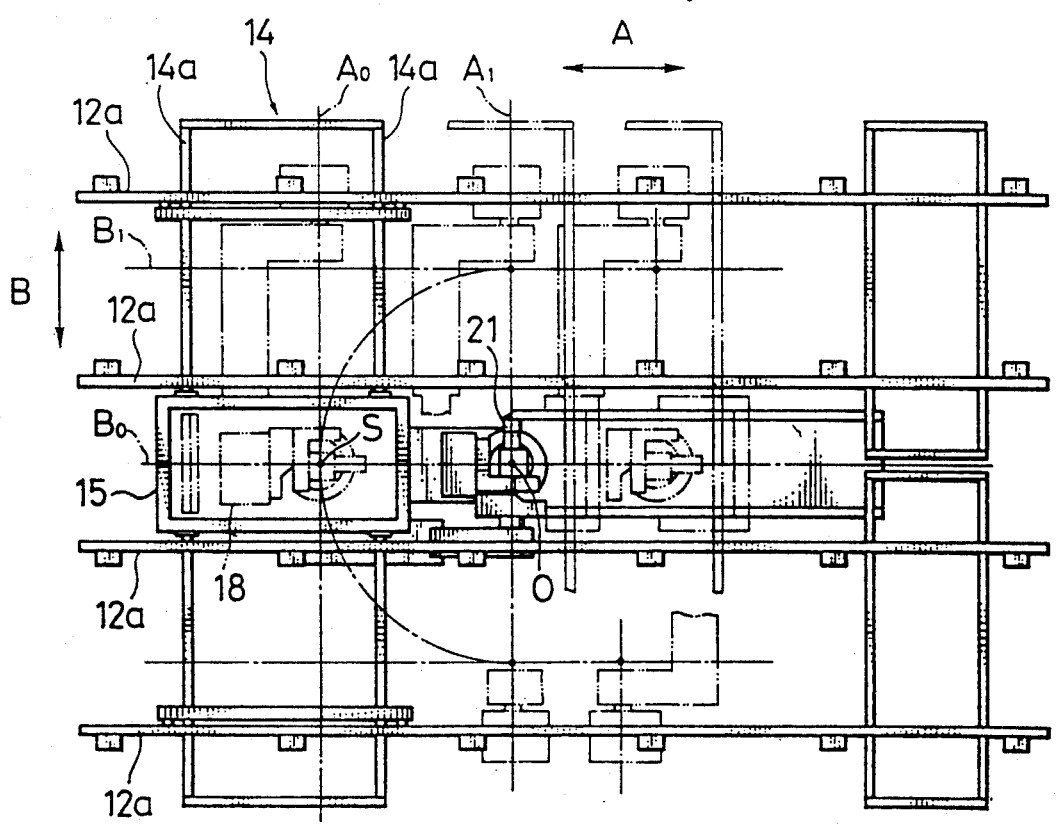
FIG. 4(B) is a top view of one embodiment of an X-ray fluoroscopic imaging apparatus according to the present invention.

Referring now to FIG. 4(A) and FIG. 4(B), one embodiment of an X-ray fluoroscopic imaging apparatus according to the present invention will be described.

This X-ray fluoroscopic imaging apparatus generally comprises a supporting arm unit 10 for supporting a fluoroscopic imaging unit 11 at positions distributed spherically around isocenter O located on a patient P lying on a bed 30, and a carrier unit 12 for moving the supporting arm unit 10 in a horizontal plane.

The supporting arm unit 10 further comprises a C-shaped arm 17 having the fluoroscopic imaging unit 11 on an upper one of its opening end and an X-ray tube unit 20 on a lower one of its opening end; an arm supporting member 16 for supporting the C-shaped arm 17 to be slidable along a circle centered around the isocenter O in a direction indicated by an arrow E; and a supporting member 18 for supporting the arm supporting member 16 to be rotatable in a vertical plane in a direction indicated by an arrow D and to be vertically movable in a direction indicated by an arrow C.

The carrier unit 12 further comprises two pairs of longitudinal guide rails 12a attached to a ceiling 13 along a length direction of the bed 30, one pair on one side of the bed 30 and the other pair on the other side of the bed 30; a sliding frame 14 capable of sliding along the longitudinal guide rails 12a in a direction indicated by an arrow A, by using its own driving motor (not shown), and having a pair of transverse guide rails 14a; and an arm suspension unit 15 capable of sliding along the transverse guide rails 14a in a direction indicated by an arrow B, by using its own driving motor (not shown), where the supporting member 18 of the supporting arm unit 10 is suspended to be rotatable around a pivotal center S which is located at a position displaced from a position of suspension of the supporting member 18, by using another driving motor (not shown) for the purpose of rotating the supporting member 18.

The fluoroscopic imaging unit 11 and the X-ray tube unit 20 are supported at two opening ends of the C-shaped arm 17 to be facing each other, and this fluoroscopic imaging unit 11 is equipped with an image intensifier 19 for converting the X-ray irradiated from the X-ray tube unit 20 into optical image signals.

Figure 5:
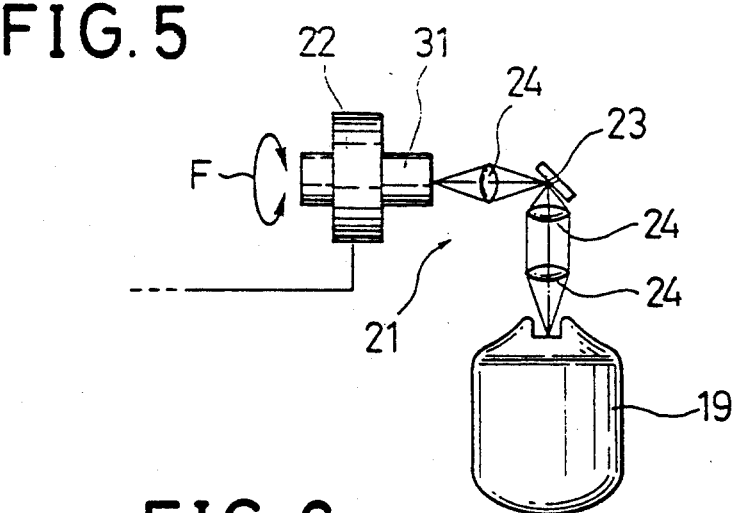
FIG. 5 is a schematic block diagram of a photoelectric conversion unit of the apparatus of FIG. 4(A).

Furthermore, as shown in FIG. 5, the image intensifier 19 is equipped with a photoelectric conversion unit 21 which includes an optical passage formed by focusing lenses 24 and a half-mirror 23 for directing the optical image signals from the image intensifier 19, a TV camera unit 31 for performing a photoelectric conversion of the optical image signals transmitted through the optical passage into electric image signals, and a camera driver unit 22 for rotating the TV camera unit 31 in a direction indicated by an arrow F.

Figure 6:
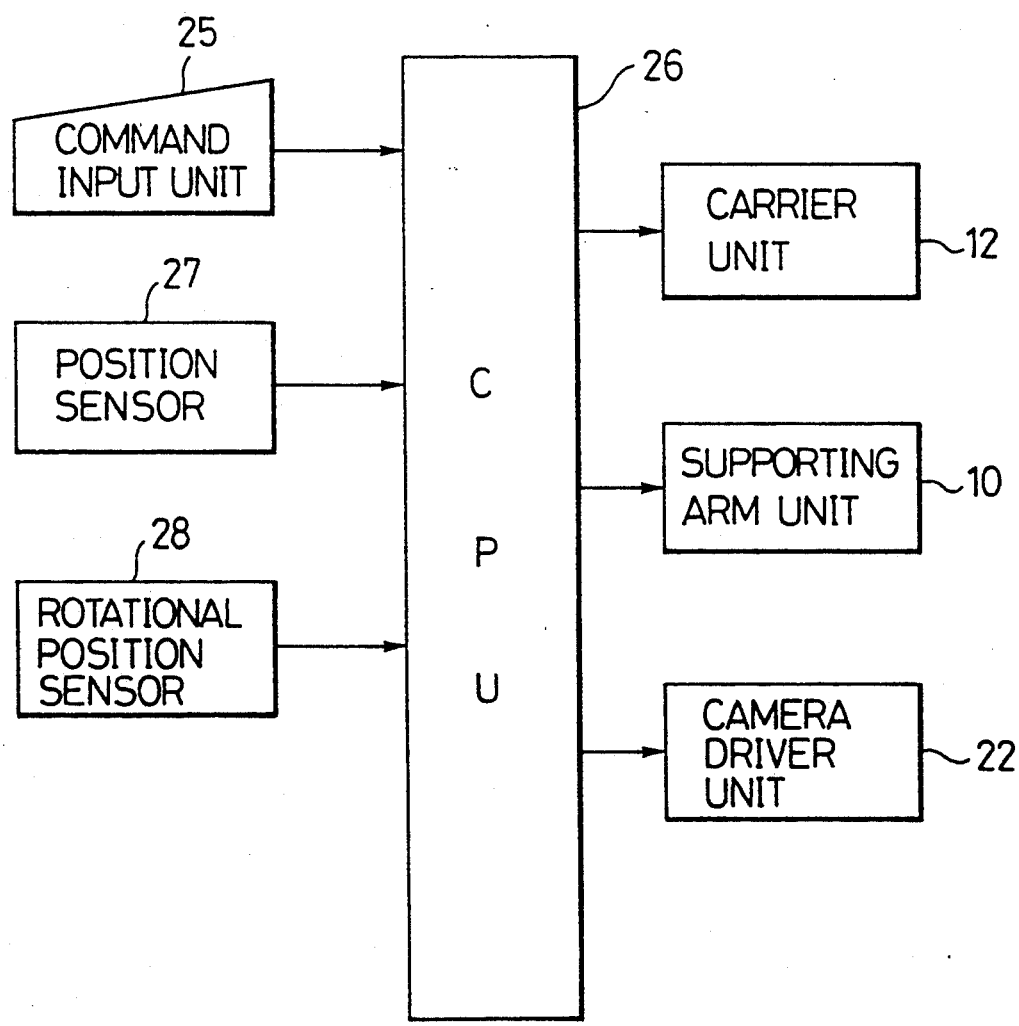
FIG. 6 is a schematic block diagram of an electrical configuration of the apparatus of FIG. 4(A).

Moreover, in terms of electrical configuration, this embodiment of an X-ray fluoroscopic imaging apparatus further comprises, as shown in FIG. 6, a command input unit 25 from which an operator enters commands to control the apparatus, a position sensor 27 for detecting a position in a horizontal plane of the supporting member 18, a rotational position sensor 28 for detecting a rotational position of the supporting member 18, all of which are connected to a CPU 26 for controlling the operation of the supporting arm unit 10, carrier unit 12, and camera driver unit 22 in accordance with the commands entered from the command input unit 25 as well as the position and rotational position detected by the position sensor 27 and rotational position sensor 28.

In this embodiment, the CPU 26 controls the supporting arm unit 10 and the carrier unit 12 such that the fluoroscopic imaging unit 11 is moved among positions distributed spherically around the isocenter O located on a patient P lying on a bed 30, so that the fluoroscopic imaging unit 11 can cover all directions around the isocenter O. This is achieved in this embodiment by combining a motion of the supporting member 18 in a horizontal plane obtained by the sliding frame 14 and the arm suspension unit 15, a rotational motion of the supporting member 18 obtained by the arm suspension unit 15, and motions of the arm supporting member 16 and the C-shaped arm 17. At the same time, the CPU 26 also controls the camera driver unit 22 in order to rotate the TV camera unit 31 by the same angle as the supporting member 18 is rotated by the carrier unit 12 but in an opposite direction.

Now, the operation of this apparatus will be described in detail.

First, the supporting arm unit 10 is placed by a head H of the patient P lying on the bed 30, with the isocenter O located at a center or region of interest such as a heart of the patient P. At this position, the fluoroscopic imaging can be performed as usual by controlling the arm supporting member 16 and the C-shaped arm 17.

Then, the supporting arm unit 10 is rotated around the isocenter O for 90° clockwise.

Namely, when the operator enters the command for this operation at the command input unit 25, the CPU 26 controls the carrier unit 12 in order to move the arm suspension unit 15 in the horizontal plane along the longitudinal and transverse guide rails 12a and 14a in the directions of the arrows A and B, and the arm suspension unit 15 in order to rotate the supporting member 18 around the pivotal center S, such that as an overall effect the supporting member 18 is rotated around the isocenter O.

Figure 7:
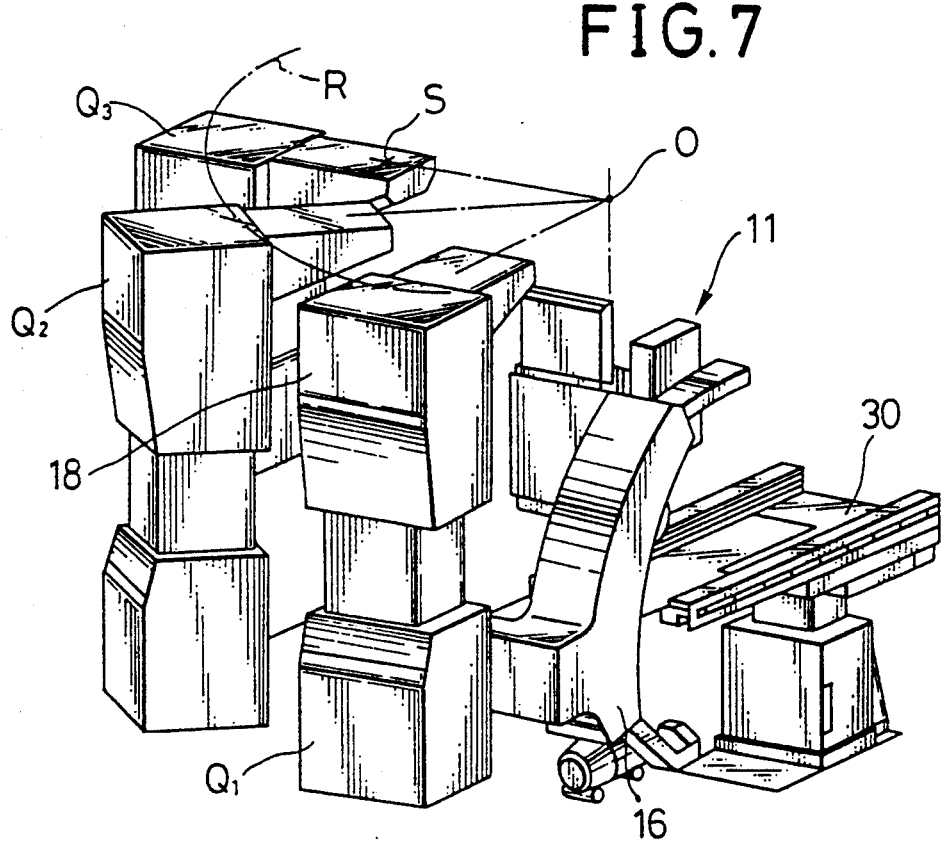
FIG. 7 is a sequential illustration of a supporting member of the apparatus of FIG. 4(A), showing its motion in a course of its operation.

That is, in FIG. 4(B), the arm suspension member 15 is moved along the transverse guide rails 14a from an initial transverse position $B_0$ to a new transverse position $B_1$ and the sliding frame 14 is moved along the longitudinal guide rails 12a from an initial longitudinal position $A_0$ to a new longitudinal position $A_1$, while the supporting member 18 is rotated around the pivotal center S by 90°. The overall motion of the supporting member 18 resulting from this operation is sequentially shown in FIG. 7, which shows that the supporting member 18 in effect rotates along a circle R around the isocenter O from an initial position $Q_1$ through an intermediate position $Q_2$ to a final position $Q_3$, throughout which the supporting member 18 is oriented toward the isocenter O.

Meanwhile, the CPU 26 also controls the camera driver unit 22 in order to rotate the TV camera unit 31 by an angle by which the supporting member 18 is rotated, but in an opposite direction from that in which the supporting member 18 is rotated, so as to maintain the orientation of the view field of the TV camera unit 31 by fixing a relative orientation of the TV camera unit with respect to the patient P. As a result of this, the orientation of the view field in the image displayed on a display unit (not shown) is unaffected by the motion of the supporting member 18, so that the quality of the diagnosis based on the displayed image is also unaffected by the motion of the supporting member 18.

At this position of the supporting member 18, the fluoroscopic imaging is carried out again by controlling the arm supporting member 16 and the C-shaped arm 17.

As a result, all the positions distributed spherically around the isocenter O can be covered by the fluoroscopic imaging unit 11, without moving the patient P himself.

It is noted that since two pairs of the longitudinal guide rails 12a are provided, the above described operation can be performed on either side of the bed 30 by changing the direction of rotation.

This feature enhances the flexibility of the apparatus in that the supporting member 18 can be placed at the preferable side of the patient P, where the preferable side is determined by the nature of the examination as well as the handedness of the doctor who conducts the examination. This flexibility is particularly significant in that a conventional fluoroscopic imaging apparatus has been often inconvenient for left-handed doctor, especially when there is a need to provide an injection of a contrast medium through a catheter. Also, in a conventional fluoroscopic imaging apparatus, the application of this operation using the catheter to the left arm of the patient P has been particularly awkward.

It is also noted that the arm supporting member 16 and the C-shaped arm 17 may be operated simultaneously with the supporting member 18, such that the fluoroscopic imaging at an arbitrary position in an arbitrary direction can be performed.

Next, the operation of this apparatus in a case of taking the fluoroscopic image of the blood vessels in the inferior limb of the patient will be described.

Figure 8:
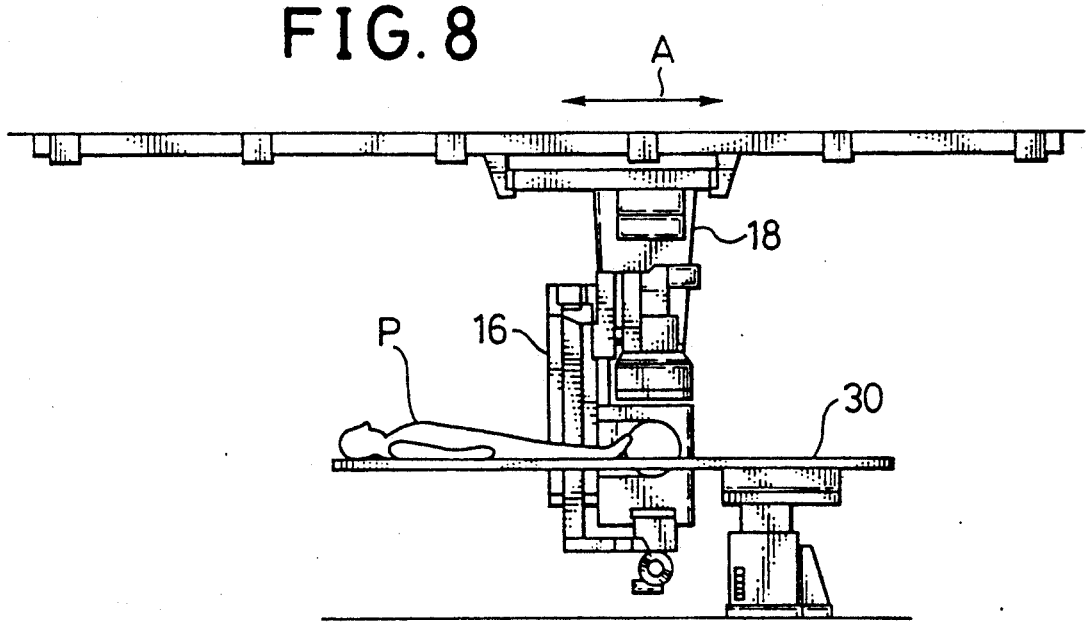
FIG. 8 is a side view of the apparatus of FIG. 4(A), showing an initial position of the supporting member in a particular type of operation.
Figure 9:
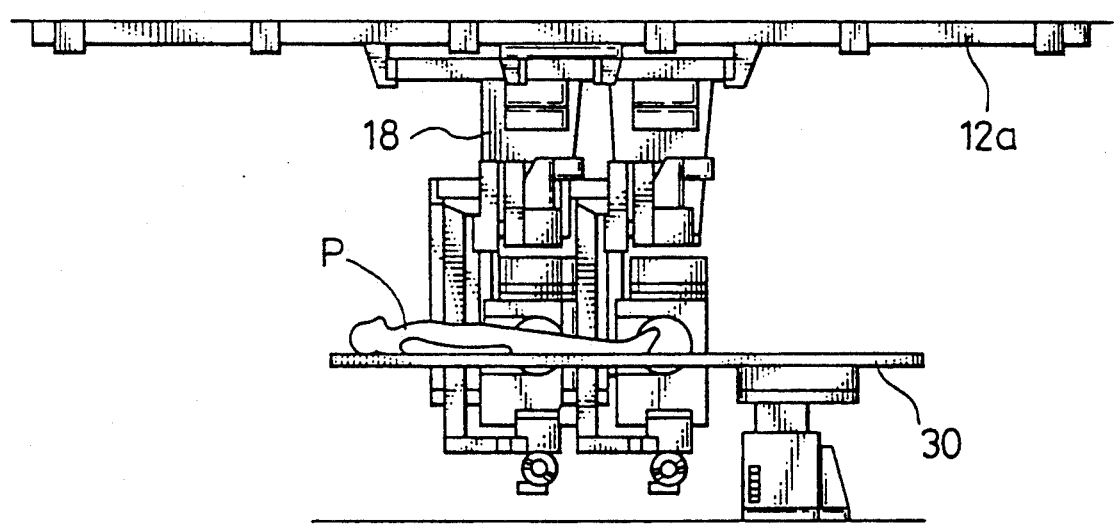
FIG. 9 is a sequential side view of the apparatus of FIG. 4(A), showing the motion of the supporting member in a particular type of operation.

In this case, the supporting member 18 is placed by the side of the patient P initially, as shown in FIG. 8, and the imaging is performed while the supporting member 18 is gradually moved step by step in the direction of the arrow A without a rotation, as shown in FIG. 9. Thus, in this embodiment, the fluoroscopic image of the blood vessels in the inferior limb can be obtained without moving the patient P himself.

It is to be noted that even in a case other than that of taking a fluoroscopic image of blood vessels in an inferior limb, it is often desirable to take an image of the entire body of a patient from head to feet, and in this embodiment, such a whole body imaging can be performed without moving the patient, by combining the two cases of operation described above.

Besides those already mentioned, many modifications and variations of the above embodiments may be made without departing from the novel and advantageous features of the present invention. Accordingly, all such modifications and variations are intended to be included within the scope of the appended claims.

What is claimed is:

1. An X-ray fluoroscopic imaging apparatus, comprising:

an arm member for supporting a fluoroscopic imaging device capable of taking a fluoroscopic image of a patient, to be slidable along a circle centered around an isocenter;

a supporting member for supporting the arm member to be rotatable in a vertical plane;

carrier means for moving the supporting member in a horizontal plane, and for rotating the supporting member in the horizontal plane around a pivotal center not identical to the isocenter, the carrier means including:

longitudinal carrier means for moving the supporting member in a longitudinal direction in the horizontal plane;

transverse carrier means for moving the supporting member in a transverse direction in the horizontal plane; and means for rotating the supporting member around the pivotal center not identical to the isocenter; and means for controlling the carrier means, the supporting member, and the arm member such that the fluoroscopic imaging device can effectively be moved among positions distributed spherically around the isocenter, without changing an orientation of the supporting member with respect to the isocenter by combining moving operations of the longitudinal carrier means and the transverse carrier means and a rotating operation of the rotating means.

2. The apparatus of claim 1, further comprising:

TV camera means for obtaining a video image from the fluoroscopic image obtained by the fluoroscopic imaging device; and means for rotating the TV camera means.

3. The apparatus of claim 2, wherein the rotating means rotates the TV camera means around a central axis of the TV camera means by an angle by which the supporting member is rotated, but in a direction opposite to that in which the supporting member is rotated.

4. The apparatus of claim 1, wherein the longitudinal carrier means can move the supporting member in the longitudinal direction on either side of the patient.

5. An X-ray fluoroscopic imaging apparatus, comprising:

a C-shaped arm member for supporting a fluoroscopic imaging device capable of taking a fluoroscopic image of a patient, to be slidable along a circle centered around an isocenter;

a supporting member for supporting the arm member to be rotatable in a vertical plane;

carrier means for linearly moving the support member in a horizontal plane, along the patient, including one pair of transverse rail members along which the supporting member is to be moved in a transverse direction across the patient and first and second pairs of longitudinal rail members along which the supporting member is to be moved in a longitudinal direction along the patient, wherein the first pair of longitudinal rail members is provided along one side of the patient while the second pair of longitudinal rail members is provided along another side of the patient, such that the arm member supported by the supporting member can be placed on either side of the patient along either of the first and second pairs of the longitudinal rail members through the transverse rail members; and means for controlling the carrier means, the supporting member, and the arm member such that the fluoroscopic imaging device can be slid along the patient on either side of the patient, with the arm member being located entirely on said either side of the patient.

* * * * *